United States Patent [19]

Yasuda et al.

[11] Patent Number: 4,523,096
[45] Date of Patent: Jun. 11, 1985

[54] LIQUID CHROMATOGRAPHY APPARATUS

[75] Inventors: Makoto Yasuda; Seiichi Murayama, both of Kokubunji, Japan

[73] Assignee: Hitachi, Ltd., Tokyo, Japan

[21] Appl. No.: 448,600

[22] Filed: Dec. 10, 1982

[30] Foreign Application Priority Data

Dec. 16, 1981 [JP] Japan .................................. 56-186348

[51] Int. Cl.³ .......................... B01D 15/08; G01J 3/00
[52] U.S. Cl. .................................. 250/373; 250/461.1; 250/493.1; 313/642; 356/72; 356/410
[58] Field of Search ............. 313/642; 250/373, 493.1, 250/461.1; 73/61.1 C; 356/72, 410, 411

[56]  References Cited

U.S. PATENT DOCUMENTS 3,720,855  3/1973  Gardner et al. ..................... 313/642
3,814,939  6/1974  Parker et al. ......................... 250/373
3,920,334  11/1975  Steichen et al. ....................... 356/72

Primary Examiner—Alfred E. Smith
Assistant Examiner—Carolyn E. Fields
Attorney, Agent, or Firm—Antonelli, Terry & Wands

[57]  ABSTRACT

A liquid chromatography apparatus comprises a detector part having as a light source a metal halide lamp filled with tantalum halide, mercury and rare gas.

3 Claims, 3 Drawing Figures

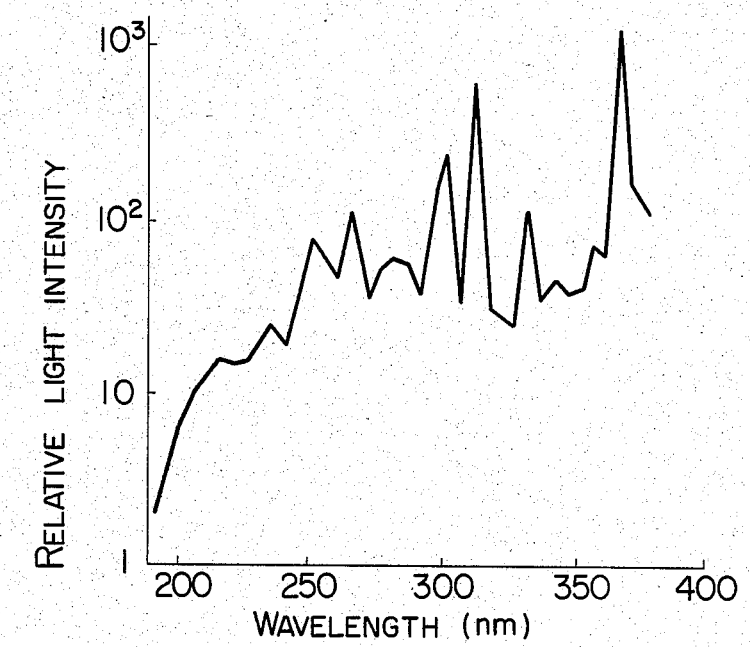
FIG. 1
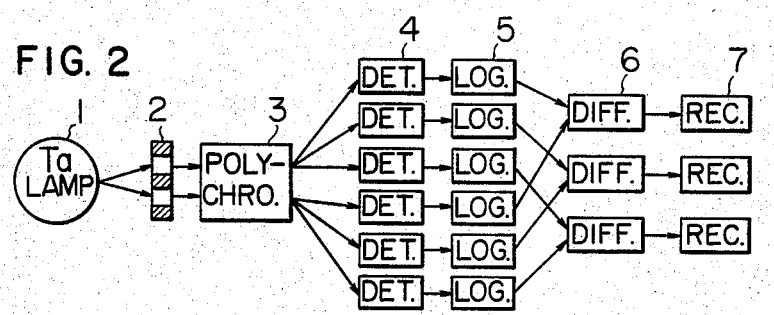
FIG. 2
FIG. 3
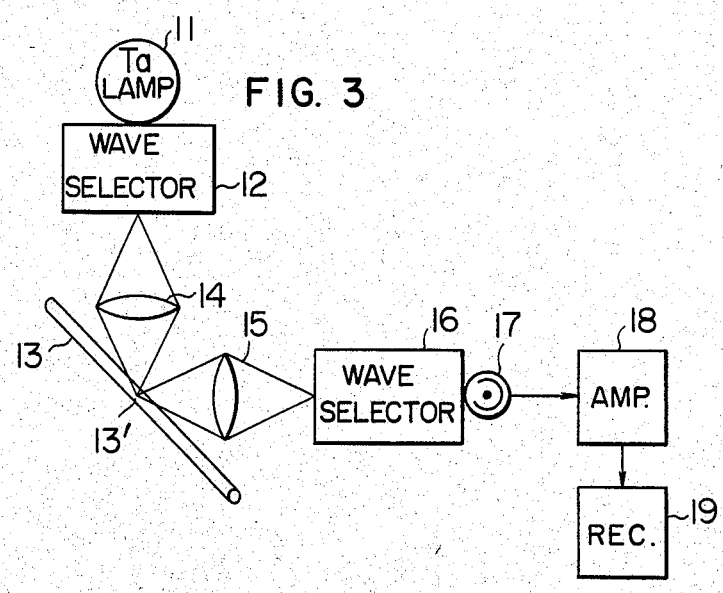

LIQUID CHROMATOGRAPHY APPARATUS

BACKGROUND OF THE INVENTION

This invention relates to improvements in liquid chromatography apparatus, and more particularly to a high-sensitivity liquid chromatography apparatus including a detector using light for analysis.

A high-sensitivity liquid chromatography apparatus includes an absorption detector, a fluorescence detector or the like using light as means for monitoring a sample separated into components in a column. Prior art liquid chromatography apparatus including such a detector using light for analysis are broadly classified into a type in which a lamp with line spectrum is employed to analyze a specific substance with high sensitivity and a universal type in which a lamp with continuum spectrum is employed so that wavelengths used for measurement can be freely selected.

Further, from the viewpoint of the principle of measurement, liquid chromatography detection using light is generally classified into two methods, that is, an absorption method and a fluorescence method.

The prior art liquid chromatography apparatus based on the absorption method is further classified into a type employing a deuterium lamp of high stability as the light source producing the continuum spectrum and a type employing a mercury lamp as the light source producing the line spectrum. When these two types are compared with each other, the sensitivity of the former type is lower than the latter type due to the weak radiance of light emitted from the deuterium lamp although the former type is suitable for universal use. While, in the case of the latter type, the wavelengths that can be used for measurement are limited to, for example, 254 nm, 297 nm, 313 nm, 365 nm, 405 nm, 436 nm, 546 nm and 579 nm at which bright lines of mercury appear although the sensitivity of the latter type is higher than the former type.

On the other hand, the prior art liquid chromatography apparatus based on the fluorescence method employs a xenon short-arc lamp emitting light of strong radiance. However, the apparatus based on the fluorescence method is defective among others in that the lamp has a short service life, and an expensive power unit is required for energizing the lamp because the lamp consumes large power and a high voltage must be applied in the starting stage.

The prior art detectors have their individual defects as pointed out above, and a novel detector free from these prior art defects is now demanded.

SUMMARY OF THE INVENTION

It is therefore a primary object of the present invention to provide a liquid chromatography apparatus including a detector which overcomes the prior art defects and which is inexpensive and operable with high sensitivity over a wide wavelength range.

In accordance with the present invention which attains the above object, there is provided a liquid chromatography apparatus comprising detector means having as a light source a metal halide lamp filled with tantalum halide, mercury and rare gas.

The present invention having the feature described above makes possible to provide an inexpensive liquid chromatography apparatus which can operate with high sensitivity over a wide wavelength range.

BRIEF DESCRIPTION OF THE DRAWINGS

FIG. 1 is a graph showing an example of the radiance of light emitted from a metal halide lamp employed in the present invention;

FIG. 2 is a block diagram of the absorption detector part in an embodiment of the liquid chromatography apparatus according to the present invention; and FIG. 3 is a block diagram of the fluorescence detector part in another embodiment of the liquid chromatography apparatus according to the present invention.

DESCRIPTION OF THE PREFERRED EMBODYMENT

The basic principle of the present invention will be first described.

From the viewpoint of universal use, it is apparent that a liquid chromatography apparatus employing a lamp with continuum spectrum is better than that employing a lamp with line spectrum. However, a lamp emitting light of a continuum spectrum and of strong radiance requires necessarily large power, and it is therefore extremely difficult to extend the service life of the lamp.

In the case of liquid chromatography, the absorption coefficient of a material which is an object of measurement has generally a gentle wavelength distribution, and the absorption is observed over a wide frequency range. Therefore, a lamp with continuum spectrum is not necessarily required.

There may be a case where some of substances subjected to measurement by liquid chromatography occupy substantially the same peak position on the chromatograph and are thus unseparable. According to a method applicable to such a case, the absorbances of the substances for light rays of different wavelengths are monitored simultaneously so as to identify the substances utilizing the fact that the absorption wavelength differs depending on the substances. In this case too, selection of the wavelength is not decisive but optional to a certain extent, and it is not necessarily required that the light source is to be a continuum-spectrum emitting lamp permitting selection of any desired wavelength.

Rather, a light source emitting a line spectrum including intense bright lines present at suitable wavelength intervals can provide high luminance with low power and has, in other words, an extended service life.

Thus, the present invention employs a detector part whose light source is a metal halide lamp containing tantalum halide, mercury and rare gas in a sealed tube. In such a metal halide lamp, emission of radiation from the molecules of tantalum halide and mercury provides a continuum spectrum in the wavelength range of 190 nm to 450 nm. Further, this metal halide lamp is suitable for the attainment of the above object since the line spectrum produced by the atoms of tantalum overlaps that produced by the atoms of mercury to further increase the radiance of light at specific wavelengths. Therefore, it is needless to mention that analysis with high sensitivity can be carried out at the wavelengths at which the bright lines of the line spectrum of mercury exist, as in the case of the prior art liquid chromatography apparatus employing the high-pressure mercury lamp. Also, because of the presence of the line spectrum of tantalum, the number of substances that can be analyzed by liquid chromatography is further increased. Furthermore, because of the presence of the continuum spectrum of strong radiance over the wide frequency range, the metal halide lamp is also applicable as a light source for a general-purpose detector part.

Thus, the apparatus according to the present invention possesses the merits of both of the prior art apparatus employing the deuterium lamp and that employing the high-pressure mercury lamp, and its sensitivity is generally equivalent to that of the prior art apparatus employing the xenon short-arc lamp so that the range of measurable substances is generally similar to that of the prior apparatus. In addition, the extended service life of the lamp facilitates maintenance of the apparatus.

When a UV absorption detector is used in the detector part of a liquid chromatography apparatus, this detector generates noise attributable to, for example, fluctuation of the light source, shot noise in the light detector and noise in the circuit. The noise attributable to fluctuation of the light source can be eliminated by taking the difference between the sample beam and a reference beam. The circuit noise can also be minimized, and the shot noise is presently the maximum cause of the final noise. The level of this shot noise N is proportional to the square root of the current value in the detector, hence, the square root of the radiance of light emitted from the light source. Since, on the other hand, the level of the signal S is proportional to the radiance, the S/N ratio is proportional to the square root of the radiance of light emitted from the light source.

FIG. 1 shows an example of the radiance of light emitted from a light source employed in the present invention. More precisely, FIG. 1 shows the radiance of light emitted from a lamp containing $TaI_5$ in a quantity of 2 mg/cm$^3$, Hg in a quantity of 6 mg/cm$^3$ and Ar at a pressure of 25 Torr in an arc tube of quartz with the arc tube loading of 46 W/cm$^2$. In FIG. 1, the integral values obtained by integration at wavelength intervals of 5 nm are plotted to represent the relative light intensity. A UV absorption detector is usable for measurement throughout the wavelength range of 195 nm to 350 nm. It will be seen from FIG. 1 that a UV absorption detector can be realized which emits light of strong radiance throughout the above wavelength range and maintains the high sensitivity over the wide wavelength range. Especially, in the case of liquid chromatography for materials such as sugar and organic acids, the short wavelength range of from 195 nm to 210 nm is most frequently used. However, because of the weak radiance of light emitted from the prior art light sources in the above wavelength range, measurement with high sensitivity could not be done in this wavelength range. The apparatus according to the present invention is especially advantageous in this point that the light source employed therein maintains its strong radiance in such a short wavelength range too thereby ensuring detection with high sensitivity.

The luminance of the light source employed in the apparatus of the present invention is equivalent to or higher than that of the Xe short-arc lamp at the wavelengths at which the line spectrum of mercury overlaps the continuum spectrum provided by radiation from the molecules of tantalum halide. Further, although the service life of the Xe short-arc lamp is quite short or only about 150 hours, the metal (Ta) halide lamp employed in the present invention has a long service life of more than 3,000 hours according to the result of a life test. The light source having such an extended service life is realized by virtue of the fact that the halogen cycle produced by the halogen contained in the arc tube acts to minimize the consumption of the electrodes and the blackening of the tube wall. For the above reasons, a liquid chromatography apparatus can be realized in which a fluorescence spectrophotometer serviceable over a long life and operable with high reliability functions as the detector.

Preferred embodiments of the liquid chromatography apparatus according to the present invention will now be described with reference to FIGS. 2 and 3.

FIG. 2 is a block diagram of an embodiment of the present invention which includes a multi-wavelength absorption detector part. Referring to FIG. 2, ultraviolet light emitted from a light source 1 passes through a dual type flow cell 2 in the form of an integral assembly of a sample cell and a reference cell and is then incident upon a polychrometer 3 to be dispersed by a diffraction grating and converted into electrical signals by a plurality of detectors 4 provided for individual wavelengths respectively. These electrical output signals from the detectors 4 are applied to associated logarithm transformers 5 to be transformed into signals linear to the absorbances respectively, and, after taking the difference between the sample beam and the reference beam in each of difference amplifiers 6, the output signals from the difference amplifiers 6 are applied to associated recorders 7 respectively. In the embodiment shown in FIG. 2, a metal halide lamp containing tantalum halide, mercury and argon in a sealed tube is employed as the light source 1, so that the S/N ratio between the signal S and the noise N can be increased and the absorption detector part can operate with high sensitivity. As described already, the metal halide lamp emits light of strong radiance and thus contributes to the realization of an absorption detector part of high sensitivity.

Further, although the light emitting part of the deuterium lamp emits light in spot-like form, the metal halide lamp employed in the present invention emits light by arc discharge between its two electrodes. Therefore, the light emitting part of the metal halide lamp can be designed to have a large axial length. Thus, the light emitting part of the metal halide lamp can be shaped to match the shape of the slits of the polychrometer 3 so that light emitted from the light source 1 can be effectively utilized.

In the optical system including the element such as the polychrometer associated with the absorption detector part, slight distortion of the optical alignment tends to occur due to, for example, variations of the room temperature, resulting in generation of noise. In the case of the metal halide lamp employed in the present invention, its light emitting area can be easily increased thereby to compensate distortion of the optical alignment and minimize the level of undesirable noise.

FIG. 3 is a block diagram of another embodiment of the present invention including a fluorescence detector part. Referring to FIG. 3, light from a light source 11, which is a metal halide lamp, passes through a wavelength selector 12, which may be a monochrometer or an interference filter, and irradiates through a condenser lens 14 a portion 13' of a sample flow path 13 in the liquid chromatography apparatus. The flow path 13 shown in FIG. 3 indicates the flow path disposed downstream of the column (not shown) in which the sample is separated into components. When a specific substance to be analyzed passes through the portion 13' of the flow path 13 irradiated with the excitation light, fluorescence appears from the specific substance. The fluorescence is focused by a focusing lens 15, passes through a second wavelength selector 16 and is converted into an electrical signal by a light detector 17 such as a photomultiplier. The output signal from the light detector 17 is amplified by an amplifier 18 before it is recorded by a recorder 19. For example, in the case of detection of an amino acid using the O-phthal-aldehyde (OPA) method, the excitation wavelength providing the highest sensitivity is between 360 nm and 365 nm and coincides with the bright line in the line spectrum of mercury. Thus, the liquid chromatography apparatus shown in FIG. 3 can operate with high sensitivity. According to the present invention in which the metal halide lamp is employed and the emitted light includes the line spectrum of tantalum, analysis of vitamin B by measurement of native fluorescence becomes possible although it was difficult to carry out such analysis by the prior art apparatus employing the high-pressure mercury lamp which does not emit light including the line spectrum of tantalum. While the center wavelength of the excitation used for the analysis of vitamin B by measurement of native fluorescence is 375 nm, the liquid chromatography apparatus of the present invention can analyze vitamin B with high sensitivity since bright lines appear at wavelengths of 372.3 nm, 373.1 nm, 373.7 nm, 375.5 nm, 375.8 nm, 375.98 nm, 376.02 nm, 376.2 nm, 377.0 nm and 377.7 nm respectively in the line spectrum of tantalum. Even in the wavelength ranges where the bright lines of tantalum and mercury are not present, the metal halide lamp can also be effectively used as the light source for the fluorescence detector since the continuum spectrum is also emitted from the lamp. In the liquid chromatography, measurement is frequently continued over several ten hours for a single batch of measurement. The xenon short-arc lamp employed hitherto for the liquid chromatography could not reliably be used for the continuous measurement over several ten hours because of its short service life. In contrast, the metal (Ta) halide lamp employed in the present invention has an extended service life and therefore contributes to the realization of a high-reliability liquid chromatography apparatus.

It will be appreciated from the foregoing description that the present invention can provide a liquid chromatography apparatus which operates with high sensitivity and is inexpensive.

We claim:

1. A liquid chromatography apparatus comprising detector means having as a light source a metal halide lamp filled with tantalum halide, mercury and rare gas.

2. A liquid chromatography apparatus according to claim 1, wherein the tantalum halide filling is $TaI_5$.

3. A liquid chromatography apparatus according to claim 1, wherein the light source emits a continuum spectrum in the wavelength range of 190 nm to 450 nm.

* * * * *